(12) United States Patent
Fagergren et al.

(10) Patent No.: US 8,002,717 B2
(45) Date of Patent: Aug. 23, 2011

(54) QUANTIFICATION OF MECHANICAL AND NEURAL CONTRIBUTIONS TO SPASTICITY

(76) Inventors: Anders Fagergren, Älta (SE); Påvel Lindberg, Paris (FR)

( * ) Notice: Subject to any disclaimer, the term of this patent is extended or adjusted under 35 U.S.C. 154(b) by 0 days.

(21) Appl. No.: 12/312,306

(22) PCT Filed: Mar. 28, 2008

(86) PCT No.: PCT/SE2008/050363
§ 371 (c)(1),
(2), (4) Date: May 5, 2009

(87) PCT Pub. No.: WO2008/121067
PCT Pub. Date: Oct. 9, 2008

(65) Prior Publication Data
US 2010/0106062 A1    Apr. 29, 2010

Related U.S. Application Data

(60) Provisional application No. 60/909,391, filed on Mar. 30, 2007.

(51) Int. Cl.
*A61B 5/103* (2006.01)
*A61B 5/117* (2006.01)
(52) U.S. Cl. .......................................... 600/595; 600/587
(58) Field of Classification Search .................. 600/300, 600/587–595; 702/127, 141–154
See application file for complete search history.

(56) References Cited

U.S. PATENT DOCUMENTS
2007/0027631 A1    2/2007    Cabrera et al.

FOREIGN PATENT DOCUMENTS
WO    WO 2006/102764    10/2006

OTHER PUBLICATIONS

International Search Report for PCT/SE2008/050363, mailed Jun. 25, 2008.
Hughes, T.A.T. et al., "An Instrument for the Bedside Quantification of Spasticity: A Pilot Study", 2001 Proceedings of the $23^{RD}$ Annual EMBS International Conference, Oct. 25-28, Istanbul, Turkey, vol. 1 of 4, pp. 1228-1231.
Lunenburger, L. et al., "Clinical Assessment Performed During Robotic Rehabilitation by the Gait Training Robot Lokomat", Proceedings of the 2005 IEEE, $9^{th}$ International Conference on Rehabilitation Robotics, Jun. 28-Jul. 1, 2005, Chicago, IL, USA, pp. 345-348.

*Primary Examiner* — Jeffrey G Hoekstra
(74) *Attorney, Agent, or Firm* — Nixon & Vanderhye P.C.

(57) ABSTRACT

The present invention relates to a system (10) operable to evaluate spasticity in a movable extremity (12). The system (10) comprises a fixation device (14) comprising a first part (14.sub.1) connected via a movable joint (16) to a second part (14.sub.2). The fixation device (14) is operable to fix the movable extremity (12) in such a way that the rotational axis of the fixation device (14) is aligned with the rotational axis of the joint of the movable extremity (12). The system (10) also comprises a moving device (18) operable to move the second part (14.sub.2) with a first, constant velocity (V.sub.1), without any reflex contribution, and with a second, constant velocity (V.sub.2) with reflex contribution. The system (10) also comprises a force sensor (20) operable to measure a first force trace in connection with the first velocity (V.sub.1), and a second force trace in connection with the second velocity (V.sub.2). The system (10) also comprises a processor means (22) connected to the force sensor (20), the processor means (22) is operable to extract a first point (P1) and second maximum point (P2) from the second force trace, and a third point (P3) from the first force trace, which three points (P1-P3) are used to evaluate spasticity.

17 Claims, 6 Drawing Sheets

|           | Kp | Pos0 | Bp | Rg | *Inertia* |
|-----------|----|------|----|----|-----------|
| P1        | —  | —    | x  | —  | x         |
| P2        | x  | x    | x  | x  | —         |
| P3        | x  | x    | —  | —  | —         |
| (P2 - P3) | —  | —    | x  | x  | —         |
| (P2 - P3) - P1 | — | — | — | x  | -x        |

QUANTIFICATION OF MECHANICAL AND NEURAL CONTRIBUTIONS TO SPASTICITY

This application is the U.S. national phase of International Application No. PCT/SE2008/050363, filed 28 Mar. 2008, which designated the U.S. and claims the benefit of U.S. Provisional Application No. 60/909,391 filed 30 Mar. 2007, the entire contents of each of which are hereby incorporated by reference.

BACKGROUND

Spasticity

Spasticity is a classical neurological symptom after brain injury. Simply, spasticity means that the resistance to passive movement in a body part increases, as muscles get stiffer and the normally inhibited stretch reflexes become hyperactive. Spasticity is also velocity dependent, so that a faster passive movement results in greater resistance to movement (Lance, 1980). It is occurs in about one fourth of all stroke patients (Sommerfeld et al, 2004; Watkins et al, 2002). Depending on the severity level it leads to functional impairments, pain, disability and reduced autonomy. Despite our lack of knowledge of the exact mechanisms, spasticity is treated with a variety of physical interventions (e.g. stretching, splinting, orthoses) and medication (e.g., botulinum toxin injections in the muscle, known as "Botox") in the clinical setting. In severe cases surgery may be indicated to help gain the joint range of motion (e.g., in spastic cerebral palsy).

There are (1) non-neural and (ii) neural components which contribute to the increased resistance to passive movement. The non-neural components include: spastic muscle cell atrophy and fibre type transformation (Dietz et at, 1986); reduced sarcomere length and changed muscle and extra cellular viscoelastic properties (O'Dwyer et al, 1996; Singer et al, 2003; Friden and Lieber, 2003; Olsson et al, 2006). Neural components include: reduced stretch reflex thresholds and increased gain of the stretch reflex (Thilmann et al, 1991; Ibrahim et al, 1993; Pierrot-Desseilligny and Burke, 2005; Nielsen et al, 2007).

Clinical Methods

Clinical practice of today lacks effective methods to reduce spasticity. Instruments which can be used for quantification of muscle tone are therefore needed. Clinical measurement of spasticity, by doctors and physical therapists, is today performed in a subjective way using a 5-point rating scale. The limb is manually moved passively, one feels the resistance and thereafter one rates it according to the Modified Ashworth rating scale (Bohannon and Smith, 1987).

The reliability of a diagnosis would increase if the clinical measurement was objective. Treatment and rehabilitation could be better targeted if the diagnosis could separate and estimate the influence of the mechanical muscle components and the neural stretch reflex components.

Experimental Studies

Early experimental studies of both the non-neural and neural components did not examine how these components related to other functional measures (Thilmann et al, 1991; Ibrahim et al, 1993). These studies used electromyography (EMG) to quantify neural activity in spasticity. However, EMG measurements are cumbersome and inter-subject comparisons remain problematic (Katz and Rymer, 1989). More recently some studies have examined the relationship between both non-neural and neural components and clinically assessed function at the ankle (Huang et al, 2006) and in the hand (Kamper et al, 2000+2003). However, these studies used specific in-house equipment (EMG and torque measures) that would be difficult to use routinely in the clinic. In addition, Kamper et al (2003) used local anaesthesia in finger muscles in order to isolate neural contribution to passive movement resistance. This method is therefore not suited as an easy-to-use clinical tool to quantify non-neural and neural contributions to increased passive movement resistance after stroke.

Experimental Studies Using Models

As there are multiple mechanical and neural factors which contribute to the passive movement resistance modelling can aid understanding of how these factors interact (Koo and Mak, 2006; He, 1998). Models have used joint position (He, 1998; Feng and Mak, 1998), EMG (Feng et al, 1999) or torque (Schmit et al, 1999; Koo and Mak, 2006) as input. Studies using joint position during passive movement indicate that posture and muscle length may effect measurements of spasticity (He, 1998) and that decreased stretch reflex thresholds and increased reflex gain may explain reduced movement during the pendulum test in the elbow in spastic patients (Feng and Mak, 1998). The importance of reflex activity was shown by Feng et al (1999) who were able to predict the passive movement trajectory by using EMG as model input. Koo and Mak (2006) performed detailed modelling of mechanical and neural factors effecting passive movement torque. A sensitivity analysis indicated that muscle spindle static gain and motoneuron pool threshold were the most sensitive parameters that could affect the stretch reflex responses of the elbow flexors. This was followed by motoneuron pool gain and spindle dynamic gain. The above results illustrate how mathematical modelling of the neuro-biomechanics at a joint is useful for understanding how mechanical and neural factors change with spasticity. However, none of the above studies investigated how the modelled factors related to function. In general, the modelling was detailed and time consuming making use of such modelling difficult in the clinical setting.

In order to develop an easy-to-use clinical spasticity measurement tool we have therefore developed a new method for separate quantification of non-neural and neural contributions to passive movement resistance. Different resistance characteristics during passive hand movements at different velocities are used to obtain values of non-neural and neural contributions via a mathematical model of the neuro-biomechanics of the human wrist (see Method for details).

The patent document US-A1-2007/0027631 describes an apparatus and method for evaluating a hypertonic condition such as spasticity in a movable extremity. The apparatus includes an accelerometer, a gyroscope, and a sensor adapted for quantifying force or pressure. The apparatus and method make use of a remote device 12 (e.g. see FIG. 5) which has a case 52, a strap 54 coupled to the case 52 so that the remote device 12 can be attached to the limb of a patient (see FIG. 6). An accelerometer 56, a gyroscope 58, and a pressure transducer 60 are mounted and connected on a circuit board 66. Also mounted and connected on the circuit board 66 are the power supply 34 and the electronic circuit devices 64 for processing and transmitting the data signals to the host processor 14.

The patent document WO-A1-2006/102764 describes a method and apparatus that advantageously measures spasticity in a reproducible way. In FIG. 1 an arm 10 is shown in which the elbow (the joint) is bent at an angle A. A joint angle sensing device such as a goniometer 12 is attached to the arm to provide angle measurements and muscle activity is monitored by an EMG 14 comprising electrodes 15. The data is processed by data processor 16 to assess spasticity by computing the angle A at which the onset of the stretch reflex (SR)

is triggered. The results may be compared to results obtained for normal individuals or individuals with similar or different diseases.

Other Patents Related to Spasticity

1. Apparatus and method for evaluating a hypertonic condition, Inventor: CABRERA MICHAEL NORMANN B (US); NORRIS JAMES A (US) Applicant: EC: IPC: G01 N33148; G01 N33/50; G01 N33148 (+1), Publication info: US2007027631-2007-02-01. [Differs from Spastiflex in the following: uses position, velocity, gyro, acceleration does not differentiate mechanical and neural contributions to muscle tone. Similarities: measures force, uses model
2. Method and apparatus for resistive characteristic assessment, Inventor: ENGSBERG JACK R (US); ENGSBERG DAVID P (US); (+1), Applicant: BARNES JEWISH HOSPITAL, EC: IPC:A61B5/22; A61B5/22, Publication info: US2007012105-200701
3. METHOD AND APPARATUS FOR DETERMINING SPASTICITY, Inventor: LEVIN MINDY (CA); FELDMAN ANATOL (CA); (+1), Applicant: VALORISATION RECH SOC EN COMMA (CA); UNIV MCGILL (CA); (+3), EC: A61B5/0488; A61B5/11, IPC: A61B5/11; A61B5/0488; A61B5/11 (+1), Publication info: WO2006102764-2006-10-05.
4. Botulinum toxins for treating muscle spasm Inventor: AOKI ROGER K (US); GRAYSTON MICHAEL W (US); (+2), Applicant: ALLERGAN INC (US), EC: IPC: A61 K38148; A61 P21102; A61K38/43 (+3), Publication info: EP1486214-2004-12-15. [Common treatment of spastic muscles]
5. METHOD FOR SIMULATION OF SPASTICITY, Inventor: KARAMYSHEV VASILIJ D (SU), Applicant: KH MED INST (SU), EC: IPC: G09B23/28; G09B23/00; (IPC1-7): G09B23/28, Publication info: SU1649599-1991-05-15 [Document available In Russian language only]
6. METHOD OF MEASURING AND RECORDING DEGREE OF LIMBS SPASTICITY, Inventor: FRANEK ANDRZEJ; GORECKI IGNACY; (+1) Applicant: GORNICZE CT REHABILITACJI LECZ (PL), EC: IPC: A61B; (IPC1-7): A61B, Publication info: PL270374-1989-01-05 15 [Descriptive documents not available]
7. Quantification of muscle tone, Uppfinnare: KANDERIAN SAMI S (US); GOLDBERG RANDAL P (US); (+4) Sökande: EC: A61B5/0488; A61B5/22D IPC: A61 B5/0488; A61B5/22; A61B5/0488 (+3), Publication information: US2002156399-2002-10-24 [Differs from Spastiflex in the following: no estimation of reflex: "moving the patient's wrist in a non-sinusoidal and non ramp trajectory and determining the stiffness, viscosity and inertial parameters using the following relationship']

SUMMARY OF THE INVENTION

The above mentioned problems are also solved with a system operable to evaluate spasticity in a movable extremity according to claim 1. The system comprises a fixation device comprising a first part connected via a movable joint to a second part. The fixation device is operable to fix the movable extremity in such a way that the rotational axis of the fixation device is aligned with the rotational axis of the joint of the movable extremity. The system also comprises a moving device operable to move the second part with a first, constant velocity without any reflex contribution, and with a second, constant velocity with reflex contribution. The system also comprises a force sensor operable to measure a first force trace in connection with the first velocity, and a second force trace in connection with the second velocity. the system also comprises a processor means connected to the force sensor, the processor means being operable to extract a first point and second maximum point from the second force trace, and a third point from the first force trace, which three points are used to evaluate spasticity.

The above mentioned problems are also solved with a method for evaluating spasticity in a movable extremity with the aid of a system according to claim 9. The method comprises the steps:

with the aid of a fixation device comprised in the system, which fixation device comprises a first part connected via a movable joint to a second part, to fix the movable extremity in such a way that the rotational axis of the fixation device is aligned with the rotational axis of the joint of the movable extremity;

to move the second part with a first, constant velocity, without any reflex contribution;

to measure a first force trace in connection with the first velocity;

to move the second part with a second, constant velocity, with reflex contribution;

to measure a second force trace in connection with the second velocity;

to extract a first and second maximum point from the second force trace; and to extract a third point from the first force trace, which three points are used to evaluate spasticity.

METHOD

Passive Movement and Resistance Measure

Subjects are positioned comfortably in supine/sitting with their hand placed and fixed in a plastic ortosis-like hand platform. Hand, fingers and forearm are fastened to allow movement only in the wrist joint. A force sensor is attached under the metacarpophalangeal joints to measure resistance to passive movement. The wrist joint is passively extended at 2 velocities (slow and fast) at constant velocity. After passively extending the wrist, there is a pause for one second before returning to the starting position. A 10 second pause separated one movement from the next. During movements the subjects are instructed to relax completely and the subjects are familiarized with the device prior to testing.

Figure 3:
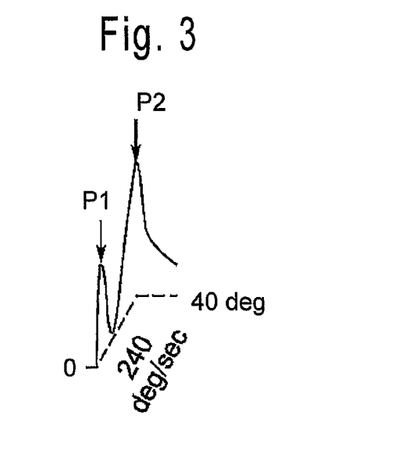
FIG. 3 discloses a schematic example of the fast movement with reflex contribution.

Three resistance measures (points) are extracted from the raw force trace:

I. P1=the highest resistance early after movement (at fast velocity) onset before 35 ms (i.e. before onset of earliest EMG activity+electromechanically delay). This point consists of force generated by moved structures i.e. muscle- and non muscle tissue acceleration, inertia, thixotropy, and viscosity (FIG. 3).

II. P2=the highest resistance after the onset of stretch reflexes (after 35 ms) and before the end of movement (at fast velocity). This point reflects a sum of muscle length-dependent and velocity-dependent muscle resistance together with velocity-dependent neural resistance (FIG. 3).

Figure 1:
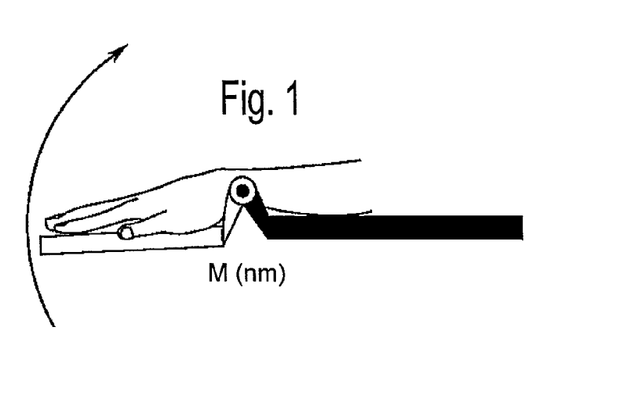
FIG. 1 discloses the principle of hand position. Resistance force is measured from e.g. the moment (M). The rotational axis of the apparatus is aligned with the rotational axis of the wrist.
Figure 2:
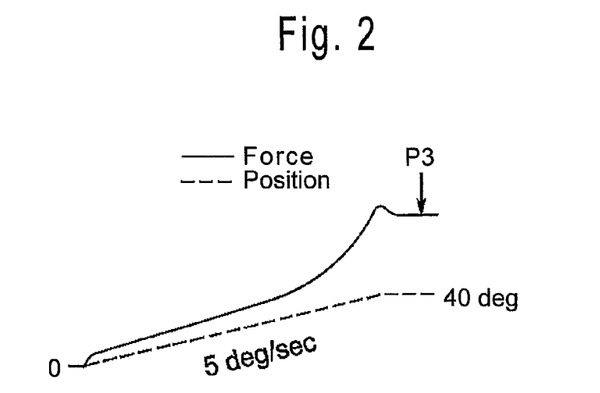
FIG. 2 discloses a schematic example of the slow movement without reflex contribution.

III. P3=the resistance at the end of a resting period (1 s) in extended position at after slow velocity movement. This point is assumed to measure the position-dependent muscle resistance as this velocity is too slow to induce neural response (i.e., <6°/s) (Schmit et al, 1999) (FIG. 2).

P1 and P3 contain passive components. P1 occurs before onset of EMG activity and P3 is measured after a slow velocity movement in order to avoid activating neural reflex (Schmit et al, 1999).

P2 contains passive (mechanical) and active (neural) components. Definition of point locations:

$$P1 = \max(F, t < 30 \text{ ms}) \text{ at } 240 \text{ deg/s}$$

$$P2 = \max(F, 30 \text{ ms} < t < t(\text{stop})) \text{ at } 240 \text{ deg/s}$$

$$P3 = F(t(\text{stop}) + 1 \text{ s}) \text{ at } 5 \text{ deg/s}$$

Parameter Estimation without Model (Point Calculations)

It is possible to retrieve separate objective measures of neural and nonneural contributions in arbitrary units directly from P1, P2 and P3. This calculation is layout in Table 1.

Non-neural contributions are reflected in P1 and P3. P1 reflects the nonneural velocity dependent resistance. P1 includes intertia which is not related to spasticity, but the inertia can be subtracted away from P1 by the product between the mass of the hand and the hand acceleration. P3 reflects the amount of position dependent resistance.

Neural contributions are reflected in P2. P2 includes velocity and position dependent components, but these can be compensated for by subtracting P3 and P1 from P2. The inertia can be compensated for the same way as in P1.

The mass of the hand could be estimated as a fraction of total body weight, e.g., 0.6% of total body weight. The acceleration at P1 is given by the apparatus specification. Thus the inertia can be regarded as a controlled and known parameter.

Model

This section provides a brief overview of the mathematical model of the neuro-biomechanics of the human wrist. The model is used for estimating the passive muscle components and the active neuronal component of the spastic hand. Below is a description of the parameters that are actually tuned to make model output fit measured data. Other parameters, e.g., hand weight and size, series element (tendons), motoneuron pool activation and deactivation dynamics and initial viscosity are held constant and are the same for all subjects. The model components and its parameters are described by Winters and Stark, 1985, 1987; Schuind et al 1994.

Non-Neural Components in the Model•Torque-Angle

Kp: the resisting force increases proportionally to the elongation of the muscle, just like an ideal spring. $F_{kp} = K_p * L$ where L is muscle length.

PosO: the resistin force increases exponentially close to maximal muscle length. $^F PosO = _e(L\ osO)_{-1}$.

Torque-Velocity

Bp: the viscous component. The resisting force increases with speed. Compare with the resisting force when transporting an object through water. $FAp = Bp/$.

Figure 4:
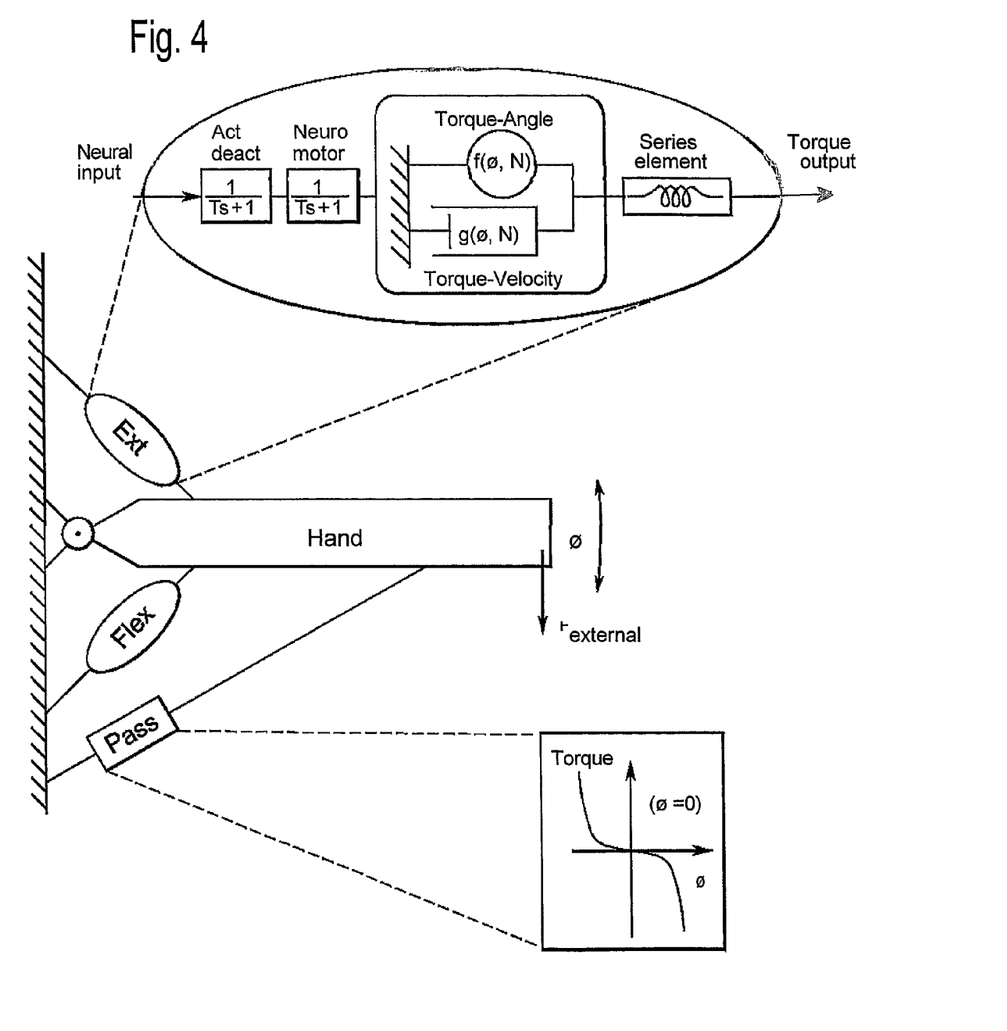
FIG. 4 discloses an illustration of the wrist model.

The contribution of the passive component is the calculated as the sum of these components: $Fp = FKp\ ^F PosO\ ^F Bp$ Inertia is also included in the model. Inertia is the force arising from the angular (rotational) acceleration of the hand. The principle of the mathematical description is the same as for a linear acceleration, $F = mdra$, where a mass accelerates along a straight line. The angular formula is simply $F = 1 \text{``a''} g$, where I is the inertia constant that includes mass and shape of the rotated object. It is important to remember that the inertia only affects the measured force and the start and the end of the ramp-hold movements since it is only at these end points there is acceleration. The movement between the end points is held at a constant velocity with no acceleration, i.e., aang=0. Note: the term "passive" is not limited to the function of the "Pass"-box in Figure but rather distinguishes from the term "active" for the reflex component.

Neuronal Component

Rg: reflex gain. A simple closed loop feedback proportional to muscle length and with a 34 ms delay. The feedback signal acts as a neural input to the muscle. The input increases proportional to muscle length. This can be compared to reflex-EMG. The initial 8-10 Hz motoneuron pool bursts, as seen in EMG data for all subjects, is not modelled.

Parameter Estimation with Model (Computer Simulations)

We use measured data to estimate the above described parameters, Bp, Kp, PosO and Rg.

Parameter Estimation with Model (Computer Simulations)

1. First, the passive components are estimated without any influence of reflex. We therefore use data from very slow ramp-hold movements that do not evoke any reflexes, see FIG. 2. Here, we fit Bp, Kp, and PosO.

2. In the next step Kp and PosO are held constant. Bp is estimated again since it seems to depend also on velocity. We tune Bp to fit the model output to the first point (P1) in the data, see FIG. 3. This is possible because P1 happens before any influence of reflex (<30 ms).

3. In the next step Bp is held constant. The reflex gain, Rg, is tuned to fit the model output to the second point (P2) in the data.

This method provides a robust way to objectively distinguish between and quantify the passive muscle components (Kp, Bp and PosO) and neuronal reflex gain (Rg).

Figure 5:
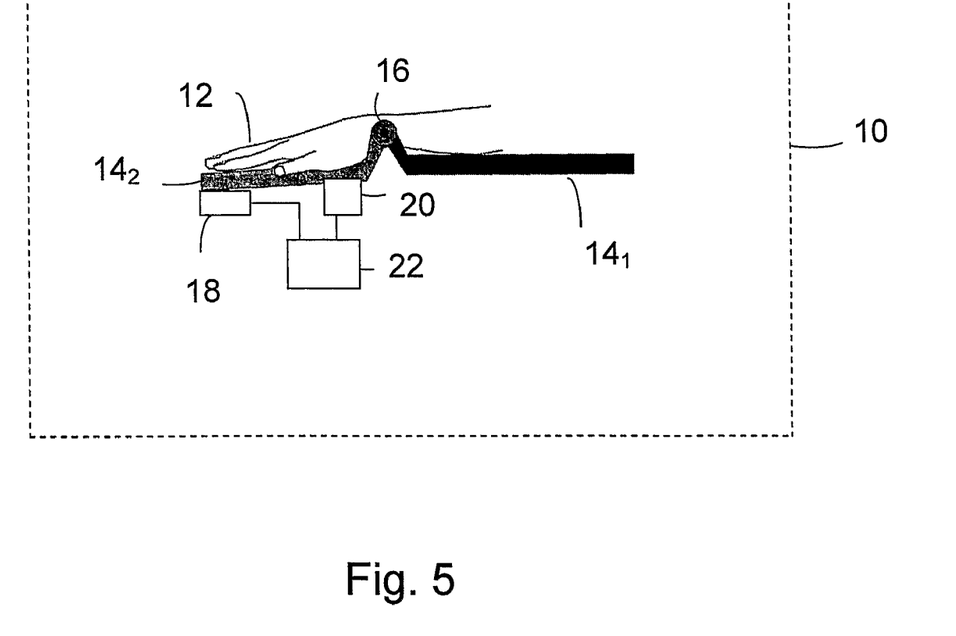
FIG. 5 discloses schematically a diagram of a system according to the present invention.

In FIG. 5 there is schematically disclosed a diagram of a system 10 operable to evaluate spasticity in a movable extremity 12. The system 10 comprises a fixation device 14 comprising a first part $14_1$ connected via a movable joint 16 to a second part $14_2$. The fixation device 14 is operable to fix said movable extremity 12 in such a way that the rotational axis of said fixation device 14 is aligned with the rotational axis of the joint of the movable extremity 12. The system 10 also comprises a moving device 18 operable to move the second part $14_2$ with a first, constant velocity $V_1$ without any reflex contribution, and with a second, constant velocity V2 with reflex contribution. The size of the movement is in the range of 40-60 degrees. A characteristic value is 50 degrees. This is valid at both velocities. The system 10 also comprises a force sensor 20 operable to measure a first force trace in connection with the first velocity $V_1$, and a second force trace in connection with the second velocity $V_2$. The system 10 also comprises a to the force sensor 20 connected processor means 22 operable to extract a first P1 and a second maximum point P2 from the second force trace, and a third point P3 from the first force trace, which three points P1-P3 are used to evaluate spasticity.

Figure 6:
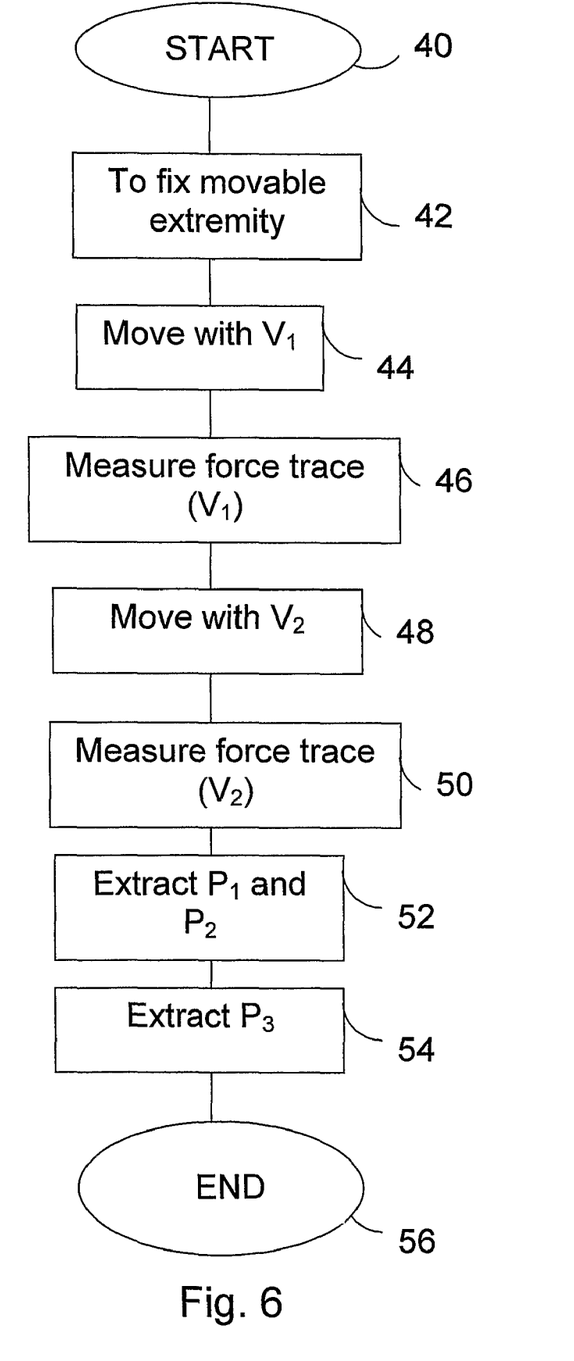
FIG. 6 is a flow chart of a method according to the present invention.

In FIG. 6 there is disclosed a flow chart of a method for evaluating spasticity in a movable extremity 12 with the aid of a system 10. The method begins at block 40. The method continues, at block 42, with the step: with the aid of a fixation device 14 comprised in the system 10, which fixation device 14 comprises a first part $14_1$ connected via a movable joint 16 to a second part $14_2$, to fix the movable extremity 12 in such a way that the rotational axis of the Fixation device 14 is aligned with the rotational axis of the joint of the movable extremity 12. Thereafter, the method continues, at block 44, with the step: to move the second part $14_2$ with a first, constant velocity $V_1$, without any reflex contribution. The method continues, at block 46, with the step: to measure a first force trace in connection with the first velocity V. Thereafter, the method continues, at block 48, with the step: to move the second part 142 with a second, constant velocity V2 with reflex contribution. The method continues, at block 50, with the step: to measure a second force trace in connection with the second velocity V2. Thereafter, the method continues, at block 52, with the step: to extract a first P1 and second maximum point P2 from the second force trace. The method continues, at block 54, with the step: to extract a third point P3 from the first force Irace, which three points P1-P3 are used to evaluate spasticity, The method is completed at block 56. It is pointed out that the step according to block 52 can be performed sometimes after block 46, and the step according to block 54 can be performed sometimes after block 50.

Figure 7:
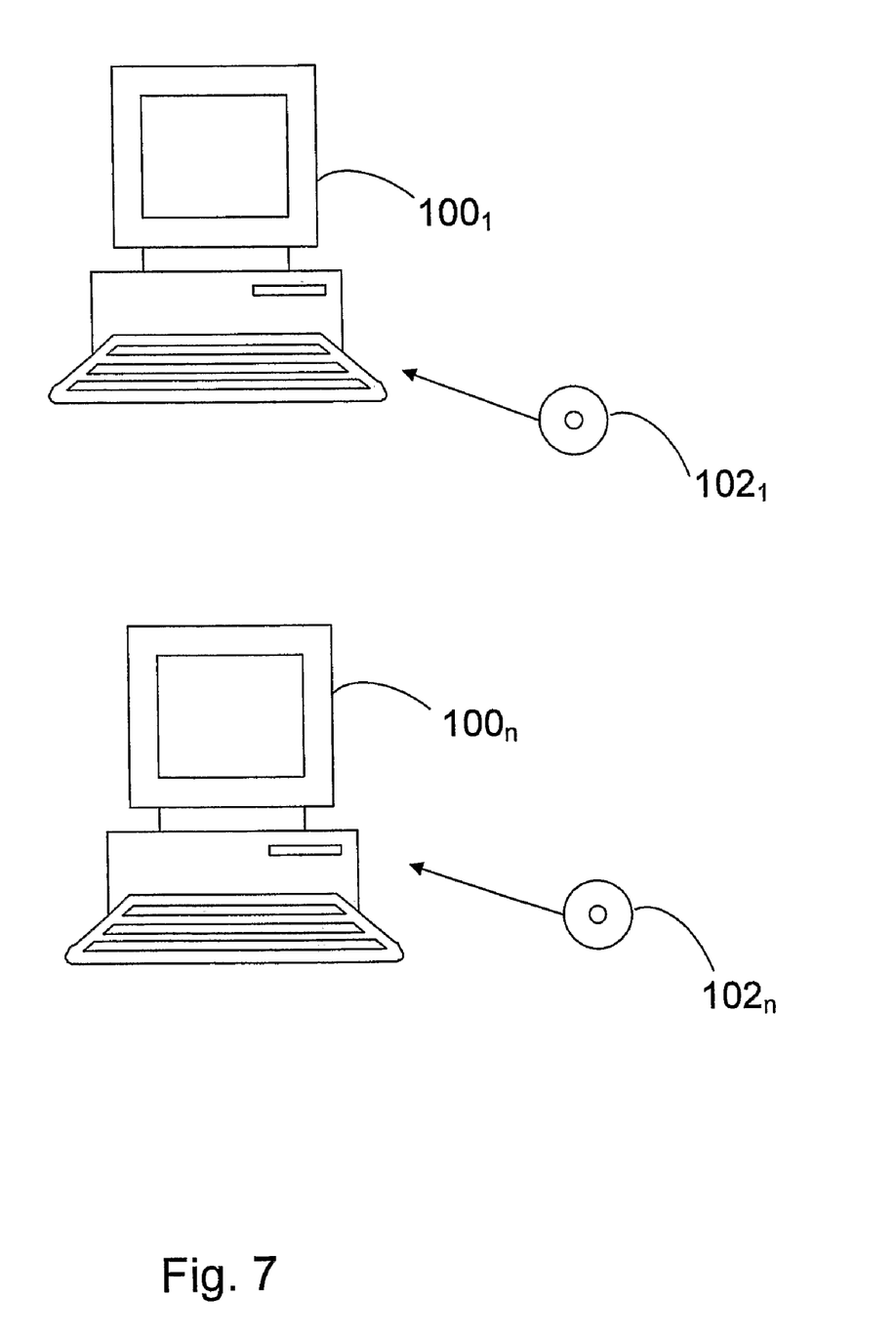
FIG. 7 discloses schematically a diagram of some computer program products according to the present invention.
Figure 8:
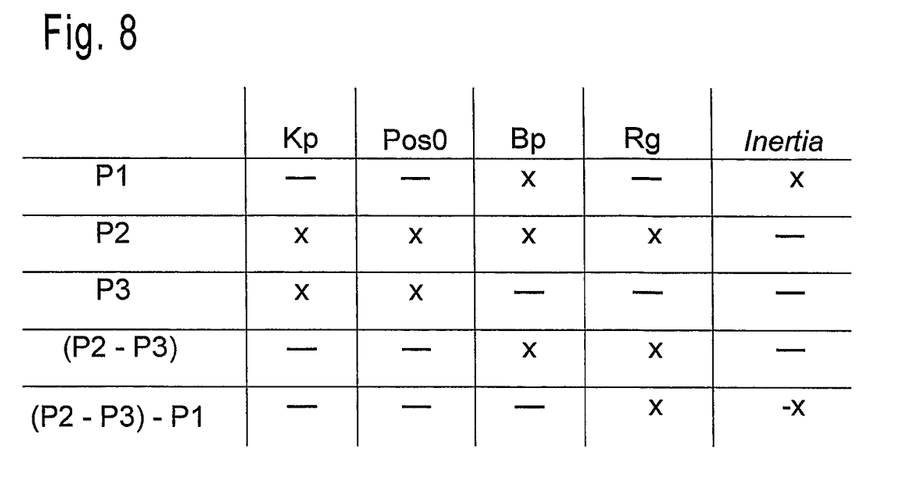
FIG. 8 is a table disclosing what parameters which affect the three defined points P1, P2 and P3. For example, Bp affects P1 and P2 but not P3.

In FIG. 7 there is disclosed a schematic diagram of some computer program products according to the present invention. There is disclosed n different digital computers $100_1, \ldots, 100_n$, wherein n is an integer. There is also disclosed n different computer program products $102_1; \ldots, 102_n$, here showed in the form of compact discs. The different computer program products $102_1, \ldots, 102_n$ are directly loadable into the internal memory of the n different digital computers $100_1, \ldots, 100_n$. Each computer program product $102_1, \ldots, 102_n$ comprises software code portions for performing some or all the steps of FIG. 6 when the product(s) $102_1 \ldots, 102_n$ is/are run on said computer(s) $100_1 \ldots, 100_n$. Said computer program products $102_1, \ldots, 102_n$ can e.g. be in the form of floppy disks, RAM disks, magnetic tapes, opto magnetical disks or any other suitable products.

The invention claimed is:

1. A system operable to evaluate spasticity in a movable extremity, said system comprising:
   a fixation device comprising a first part connected via a movable joint to a second part, the fixation device being operable to fix said movable extremity in such a way that the rotational axis of said fixation device is aligned with the rotational axis of the joint of the movable extremity,
   a moving device operable to move said second part with a first, constant velocity ($V_1$) without any reflex contribution, and with a second, constant velocity ($V_2$) with reflex contribution,
   a force sensor operable to measure a first force trace in connection with said first velocity ($V_1$), and a second force trace in connection with said second velocity ($V_2$),
   a processor means connected to said force sensor and operable to extract three resistance measurements from the first and second force traces, the three resistance measurements being a first point (P1) and second maximum point (P2) extracted from said second force trace, and a third point (P3) extracted from said first force trace, the three points (P1, P2 and P3) being used to evaluate spasticity based on non-neural contributions to passive movement resistance being reflected in (P1) and (P3) and neural contributions to passive movement resistance being reflected in (P2).

2. The system according to claim 1, wherein said moving device also is operable to, after having moved said second part with said first velocity ($V_1$) or with said second velocity ($V_2$), hold said second part during a first predetermined time interval ($t_1$) before moving said second part to a starting position, wherein said third point (P3) is measured during said first predetermined time interval ($t_1$).

3. The system according to claim 2, wherein said moving device also is operable to hold said second part during a second predetermined time interval ($t_2$) before starting moving said second part with said second velocity ($V_2$).

4. The system according to claim 3, wherein said first velocity ($V_1$) is in the range of 1-40 degrees/second, and said second velocity ($V_2$) is in the range of 100-400 degrees/second.

5. The system according to claim 4, wherein said first velocity ($V_1$) is 5 degrees/second, and said second velocity ($V_2$) is 240 degrees/second.

6. The system according to claim 5, wherein said force sensor is arranged under said movable extremity.

7. The system according to claim 5, wherein said force sensor is arranged in connection with the rotational axis of said fixation device.

8. The system according to claim 6, wherein the resistance measurements corresponding to said three points (P1, P2 and P3) are defined as P1=max F at t<35 ms at said second velocity ($V_2$), P2=max F at 35 ms<t<t (stop) at said second velocity ($V_2$), and P3=F at t (stop)+1 s at said first velocity ($V_1$), where "F" is force, "t" is the time of the respective resistance measurements, and "t (stop)" is the moment in time when said second part has stopped moving.

9. A method for evaluating spasticity in a movable extremity with the aid of a system comprising a fixation device comprising a first part connected via a movable joint to a second part, a moving device, a force sensor and a processor means connected to said force sensor, the method comprising the steps of:
   using the fixation device to fix said movable extremity in such a way that the rotational axis of said fixation device is aligned with the rotational axis of the joint of the movable extremity;
   using the moving device to move said second part with a first, constant velocity ($V_1$), without any reflex contribution and to move said second part with a second, constant velocity ($V_2$), with reflex contribution;
   using the force sensor to measure a first force trace in connection with said first velocity ($V_1$) and a second force trace in connection with said second velocity ($V_2$);
   using the processor means connected to said force sensor to extract three resistance measurements from the first and second force traces, the three resistance measurements being a first point (P1) and second maximum point (P2) extracted from said second force trace, and a third point (P3) extracted from said first force trace, the three points (P1, P2 and P3) being used to evaluate spasticity based on non-neural contributions to passive movement resistance being reflected in (P1) and (P3) and neural contributions to passive movement resistance being reflected in (P2).

10. The method for evaluating spasticity in a movable extremity according to claim 9, wherein said method also comprises the steps of:
- after said second part has been moved with said first velocity ($V_1$) or with said second velocity ($V_2$), holding said second part during a first, predetermined time interval ($t_1$), before moving said second part to a starting position; and
- measuring said third point (P3) during said first, predetermined time interval ($t_1$).

11. The method for evaluating spasticity in a movable extremity according to claim 10, wherein said method also comprises the step of holding said second part during a second, predetermined time interval ($t_2$) before starting to move said second part with said second velocity ($V_2$).

12. The method for evaluating spasticity in a movable extremity according to claim 11, wherein said first velocity ($V_1$) is in the range of 1-40 degrees/second, and said second velocity ($V_2$) is in the range of 100-400 degrees/second.

13. The method for evaluating spasticity in a movable extremity according to claim 12, wherein said first velocity ($V_1$) is 5 degrees/second, and said second velocity ($V_2$) is 240 degrees/second.

14. The method for evaluating spasticity in a movable extremity according to claim 13, wherein said measurements of said force traces are performed using the force sensor with the force sensor arranged under said movable extremity.

15. The method for evaluating spasticity in a movable extremity according to claim 13, wherein said measurements of said force traces are performed using the force sensor with the force sensor arranged in connection with the rotational axis of said fixation device.

16. The method for evaluating spasticity in a movable extremity according to claim 14, wherein the resistance measurements corresponding to said three points (P1, P2 and P3) are defined as P1=max F at t<35 ms at said second velocity ($V_2$), P2=max F at 35 ms<t<t (stop) at said second velocity ($V_2$), and P3=F at t (stop)+1 s at said first velocity ($V_1$), where "F" is force, "t" is the time of the respective resistance measurements, and "t (stop)" is the moment in time when said second part has stopped moving.

17. At least one computer program product ($102_1, \ldots, 102_n$) directly loadable into an internal memory of at least one digital computer ($100_1, \ldots, 100_n$), comprising software code portions for performing the steps of claim 9 when said at least one product ($102_1, \ldots, 102_n$) is/are run on said at least one computer ($100_1, \ldots, 100_n$).

* * * * *